(12) United States Patent
Mireshghi (10) Patent No.: US 9,687,193 B2
(45) Date of Patent: Jun. 27, 2017

(54) SLEEP APNEA AVOIDANCE AND DATA COLLECTION DEVICE

(71) Applicant: Ali Mireshghi, Saratoga, CA (US)

(72) Inventor: Ali Mireshghi, Saratoga, CA (US)

(*) Notice: Subject to any disclaimer, the term of this patent is extended or adjusted under 35 U.S.C. 154(b) by 201 days.

(21) Appl. No.: 13/763,625

(22) Filed: Feb. 9, 2013

(65) Prior Publication Data

US 2014/0228711 A1    Aug. 14, 2014

(51) Int. Cl.
*A61B 5/00* (2006.01)
*A61B 5/11* (2006.01)
*A61B 5/103* (2006.01)
*A61F 5/56* (2006.01)
*A61M 21/00* (2006.01)
*A61N 1/36* (2006.01)

(52) U.S. Cl.
CPC ......... *A61B 5/4818* (2013.01); *A61B 5/1116* (2013.01); *A61B 5/4836* (2013.01); *A61B 5/6833* (2013.01); *A61B 5/7405* (2013.01); *A61B 5/746* (2013.01); *A61B 5/7455* (2013.01); *A61F 5/56* (2013.01); *A61M 21/00* (2013.01); *A61B 5/002* (2013.01); *A61B 5/6898* (2013.01); *A61B 2560/0214* (2013.01); *A61B 2562/0247* (2013.01); *A61M 2021/0022* (2013.01); *A61M 2021/0072* (2013.01); *A61M 2205/18* (2013.01); *A61M 2205/332* (2013.01); *A61M 2205/3561* (2013.01); *A61M 2205/3569* (2013.01); *A61M 2205/3592* (2013.01); *A61M 2205/505* (2013.01); *A61M 2205/52* (2013.01); *A61M 2205/8206* (2013.01); *A61M 2205/8243* (2013.01); *A61M 2209/088* (2013.01); *A61M 2230/62* (2013.01); *A61N 1/3601* (2013.01)

(58) Field of Classification Search
None
See application file for complete search history.

(56) References Cited

U.S. PATENT DOCUMENTS

| | | | | |
|---|---|---|---|---|
| 4,715,367 A | * | 12/1987 | Crossley | A61B 5/113 600/27 |
| 5,123,425 A | * | 6/1992 | Shannon, Jr. | A61B 5/113 128/848 |
| 5,438,719 A | * | 8/1995 | Anthony | A47G 9/02 5/485 |
| 6,368,287 B1 | * | 4/2002 | Hadas | A61B 5/0878 600/529 |
| 6,666,830 B1 | * | 12/2003 | Lehrman | A61B 7/003 600/529 |
| 2002/0002326 A1 | * | 1/2002 | Causey et al. | 600/300 |
| 2002/0016568 A1 | * | 2/2002 | Lebel | A61M 5/172 604/131 |
| 2007/0103110 A1 | * | 5/2007 | Sagoo | 320/109 |

(Continued)

*Primary Examiner* — Devin Henson
*Assistant Examiner* — Matthew Kremer (57) ABSTRACT

A device for sleep apnea avoidance and data collection may include a sensor configured to sense a pressure and generate a first signal when the pressure exceeds a threshold. A signal generator module may be configured to generate a first stimulating signal in response to the first signal. The sensed pressure may include a pressure exerted on the sensor when a user of the device lies down on the device. The first stimulating signal may be configured to cause the user to change sleeping position, for example, from a first sleeping position that causes snoring to a second sleeping position that stops snoring.

20 Claims, 5 Drawing Sheets

(56) References Cited

U.S. PATENT DOCUMENTS

| | | | |
|---|---|---|---|
| 2008/0015457 A1* | 1/2008 | Silva | A61B 5/4818 |
| | | | 600/534 |
| 2008/0275349 A1* | 11/2008 | Halperin et al. | 600/484 |
| 2010/0217345 A1* | 8/2010 | Wolfe | A61B 5/024 |
| | | | 607/17 |
| 2011/0295083 A1* | 12/2011 | Doelling et al. | 600/301 |
| 2013/0165809 A1* | 6/2013 | Abir | A61B 5/1126 |
| | | | 600/534 |

* cited by examiner

SLEEP APNEA AVOIDANCE AND DATA COLLECTION DEVICE

FIELD

The disclosure relates in general to sleep disorder prevention, and more particularly to, a sleep apnea avoidance and data collection device.

BACKGROUND

Many people suffer from sleep disorder that can make them feel tired the next day, even after a full night sleep. Sleep apnea may be a potentially serious sleep disorder and may include obstructive sleep apnea or central sleep apnea. The obstructive sleep apnea may occur when throat muscles relax and makes breathing difficult. In the central sleep apnea, on the other hand, the brain may stop sending proper signals to the muscles that control breathing. Sleep apnea, in particular, the obstructive sleep apnea, which is more common, may be recognized by one or more symptoms, for example, loud snoring.

Obstructive sleep apnea may be attributed to excess weight, especially fat deposits around upper airways, a narrowed airway, family history, age, race, and other factors. Most people with obstructive sleep apnea symptoms such as snoring may by sleeping in a particular position that, for example, the relaxed throat muscles can partially block the airway. For instance, in many people snoring may occur when they sleep on their back and if they change sleeping position and sleep on their sides, the snoring may stop. Therefore, there is a need for a device that can cause a sleeping person to change sleeping position, even without being awakened.

SUMMARY

In one aspect, a device for sleep apnea avoidance and data collection may include a sensor configured to sense a pressure and generate a first signal when the pressure exceeds a threshold. A signal generator module may be configured to generate a first stimulating signal in response to the first signal. The sensed pressure may include a pressure exerted on the sensor when a user of the device lies down on the device. The first stimulating signal is configured to cause the user to change sleeping position, for example, from a first sleeping position that causes snoring to a second sleeping position that stops snoring.

In another aspect, a method for sleep apnea avoidance and data collection may include configuring a sensor to sense a pressure and to generate a first signal when the pressure exceeds a threshold. A signal generator module may be configured to generate a first stimulating signal in response to the first signal. The first stimulating signal may be configured to cause the user to change sleeping position, from a first sleeping position that causes snoring to a second sleeping position that stops snoring. The sensed pressure may include a pressure exerted on the sensor when a user of the device lies down on the device.

In yet another aspect, a device for communicating with a sleep apnea avoidance device may include a communication module configured to wirelessly communicate with the sleep apnea avoidance device. An interface module may be configured to provide one or more user interfaces. The user interfaces may be configured to receive user inputs from a user including a user of the sleep apnea prevention device. The user inputs may be used for communication to the sleep apnea avoidance device. The user interfaces may display information received from the sleep apnea avoidance device.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

In one or more implementations, the subject technology provides a method and device for sleep apnea avoidance and collection of information related to the sleeping habits of a user of the sleep apnea avoidance device. The device may be used while the user is sleeping and may help the user to change sleeping position from a first sleeping position, in which the user indicates a sleep apnea symptom such as snoring, to a second sleeping position. The device may be capable of communicating with another device of the user such as a handheld wireless communication device.

Figure 1A:
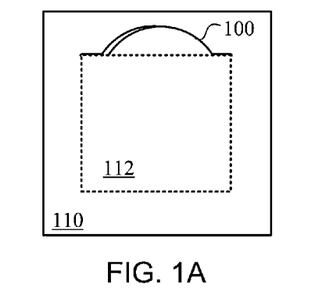
FIGS. 1A-1B are conceptual diagrams illustrating examples of a device for sleep apnea avoidance and data collection.
Figure 1B:
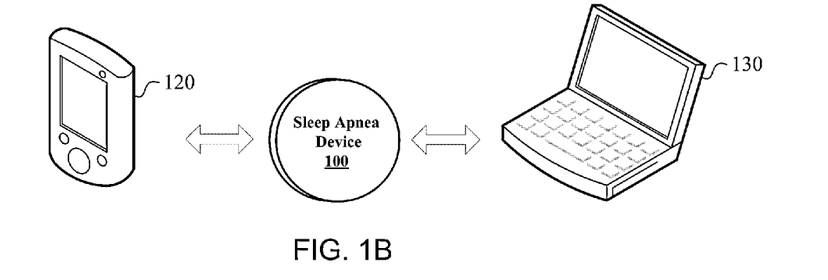

FIGS. 1A-1B are conceptual diagrams illustrating examples of a device 100 for sleep apnea avoidance and data collection. In the diagram shown in FIG. 1A, the device 100 is illustrated to be used in a pocket 112 of a pad 110. The pad 110 may be wearable by the user, for example, may have an adhesive layer, for instance, on the back of the pad 110, which can allow the pad 110 to be safely adhered to and removed from the human skin, similar to the existing wound bandages. The pad 110 may be adhered to any part of the body, in particular on the part of the body that when the user sleep on that part, sleep apnea symptoms such as snoring happens, for example, on the back of the user. It is understood that many people have sleep apnea symptoms (e.g., snoring) when sleeping on their back.

In one or more aspects, the device 100 may be worn in a pocket of an under-wear such as a T-shirt, sleepwear, and the like. The pocket may be on a suitable position on the under-wear, for example, on the back of the under-wear, if the user snores when sleeping on her/his back. The device 100, although shown as a thin disk, may be built in any shape and size that would be comfortable to wear when sleeping. In one or more implementations, the device 100 may be built in a flat form with various shapes and may have a thin (e.g., a few mms) and flexible packaging.

In one or more implementations, as shown in FIG. 1B, the device 100 may be able to communicate with another device (e.g., an external device), for example, a handheld device 120 such as a wireless communication device including a mobile phone, a personal digital assistant (PDA), a tablet, a phablet, or a personal computer 130 such as a laptop and the like. The device 100 may be configured to collect data including history information related to the use of the device 100 by the user, and to communicate the collected data to the other device. The device 100 may also be able to receive from the other device user input information. The device 100 may be able to communicate with the other device through a wireless network, such as Wi-Fi, WLAN, PAN, WAN, and the like, via near-field-communication (NFC), or other network technologies. In one or more implementations, the device 100 may include a rechargeable battery that can be wirelessly charged from the other device, for example, the handheld device 120 or the personal computer 130.

Figure 2A:
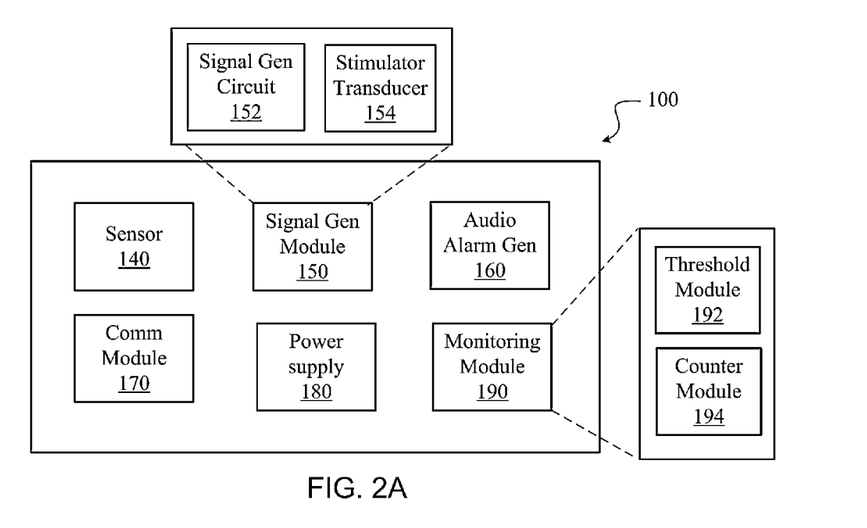
FIG. 2A is a block diagram illustrating an example structure of the device for sleep apnea avoidance and data collection of FIGS. 1A and 1B.

FIG. 2A is a block diagram illustrating an example structure of the device 100 for sleep apnea avoidance and data collection of FIGS. 1A and 1B. The device 100 may include, but not be restricted to, a sensor 140, a signal generator (also called "signal generator module") 150, an audio alarm generator 160, a communication (also called "communication module") 170, a power supply 180, and a monitoring module 190. The monitoring module 190 may include a threshold generator (also called "threshold generator module") 192 and a counter also called "counter module") 194. The sensor 140 may include a pressure sensor, such as a thin film pressure sensor, for example, a piezoelectric, piezo-resistive, capacitive, electromagnetic, optical, or other type of pressure sensor. In one or more implementations, the sensor 140 may be integrated with other electronic components of the device 100 such as the signal generator module 150, communication module-170, monitoring module 190, and other electronic components, for example, on a the same chip (e.g., a semiconductor chip, such as a silicon chip).

The sensor 140 may be configured to sense a pressure exerted on the sensor when a user lies down on the device 100. The sensor 140 may generate, in response to the sensed pressure exceeding a threshold, a first signal that is received by the signal generator module 150. The threshold may be set by the user through a user interface of the other device (e.g., the handheld device 120 or the personal computer 130). In an aspect, the threshold module 192 may be configured to set (e.g., generate) the threshold when the user lies down on the device for a first time, on a designated bed (e.g., a user's bed). For example, the user may inform the device 100, using the other device, when the user uses the designated bed and lies down, for the first time, on the device 100. This is because the pressure exerted on the sensor 140 may depend on the softness/firmness of the bed that the user is using.

In one or more aspects, the user may set the threshold through a user interface of the other device (e.g., handheld device 120). The other device 100 may communicate the threshold setting to the device 100, where the threshold module 192 receives the threshold setting communicated by the other device and uses the threshold setting to set the threshold of the sensor 140. The threshold may be changed by the user, for example, when the user becomes more sensitive to the first signal or when the softness/firmness of the bed may change. In some aspects, the threshold may be set or changed from the device 100.

The signal generator module 150 may generate, in response to the first signal, a first stimulating signal, which may cause the user to change sleeping position. The signal generator module 150 may include a signal generator circuit 152 and a stimulator transducer 154. The signal generator circuit 152 may generate the first stimulating signal that includes electrical signals such as electrical pulses that are applied to the stimulator transducer 154. The first stimulating signal may include different types, each type, for example, identified by a specific signal waveform, such as rectangular, sawtooth, triangular, pulse, and the like. The first stimulating signal may also have attributes including, but not limited to, frequency, duty cycle, and magnitude. The signal generator circuit 152 may stop generating the first stimulating signal in response to a stop signal from the sensor 140 when the user changes sleeping position from a first sleeping position that causes snoring to a second sleeping position that stops snoring. The signal generator module 150 may generate the first stimulating signal based on the information related to the selected stimulating signal received from the other device (e.g., the handheld device 120 or the personal computer 130 of FIG. 1B). The user may employ a user interface (e.g., a second user interface) on the other device to input information related to a selected first stimulating signal including, but not limited to, the type, the magnitude, the frequency, and the duty cycle.

The stimulator transducer 154 may use the stimulating signals (e.g., the first stimulating signal) to generate vibrational or tickling stimuli that can make the user change sleeping position. The stimulator transducer 154 may be similar to or be the same as the sensor 140, which can have dual functionality and work as both a pressure sensor and a stimulator transducer. For example, a piezoelectric thin film may be able to have the dual functionality of a pressure sensor and a stimulator transducer. In one or more aspects of the subject technology, the stimulating transducer 154 may be separate from the sensor 140.

The counter module 194 may start measuring an elapsed time in response to the first signal, and may generate a first change signal when the elapsed time reaches a first preset value. The counter module 194 may generate a second change signal when the elapsed time reaches a second preset value. The first and the second preset values may be set by the user by employing a user interface of the other device. The signal generator module 150 may generate a second stimulating signal and a third stimulating signal in response to the first and second change signals received from the counter module 194. The information related to the second and third stimulating signals and the first and second preset values may be received from the other device. The user may provide the information related to the second and third stimulating signals and the first and second preset values through one or more user interfaces of the other device. The second and third stimulating signals, similar to the first stimulating signal, may be identified by a number of attributes including, but not limited to, a frequency, a duty cycle, a magnitude, and a type, as described above.

The audio alarm generator 160 may generate an audio alarm signal based on the information related to an audio alarm signal received from the other device. The information related to the audio alarm signal may include, but not limited to, a type, a volume, and a trigger event. The trigger event may indicate a trigger event for activating the audio alarm signal. For example, the trigger event may include non-responsiveness of the user to the first, second and third stimulating signals. That is to say, if the user did not change position in response to the stimuli generated as the result of the first, second, and third stimulating signals, the monitoring module 190 may send a trigger signal to the audio alarm generator 160 to start an audio alarm signal that may awaken the user. It is understood that the attributes of the first, second, and third stimulating signals may be set by the user so that these stimulating signal does not awaken the user and just make the user to change position.

The communication module 170 may include a wireless transmitter that can communicate with the other device via a wireless network, such as Wi-Fi, WLAN, PAN, WAN, and the like, via near-field-communication (NFC), or other network technologies. For example, the communication module 170 may be configured to receive information from the other device. The information received from the other device may include information related to a use of a bed including the information indicating the bed as the designated bed and the first time that the designated bed is used by the user. The information may include information related to the threshold set by the user using a first interface on the other device, the selected first stimulating signal, the audio alarm signal.

The communication module 170 may be configured to transmit to the other device history information. The history information may be stored in the other device and may be displayed to the user upon request. The history information may include a date, a start time and a stop time for each of the first, second, and third stimulating signals, and the audio alarm signals that were generated, each time the device was used by the user.

The power supply module 180 may include a voltage regulator and a power source such as battery, including a rechargeable battery. The voltage regulator may provide the electrical power for device 100. In one or more implementation, the rechargeable battery of the power supply 180 may be wirelessly rechargeable from, for example, the other device.

Figure 2B:
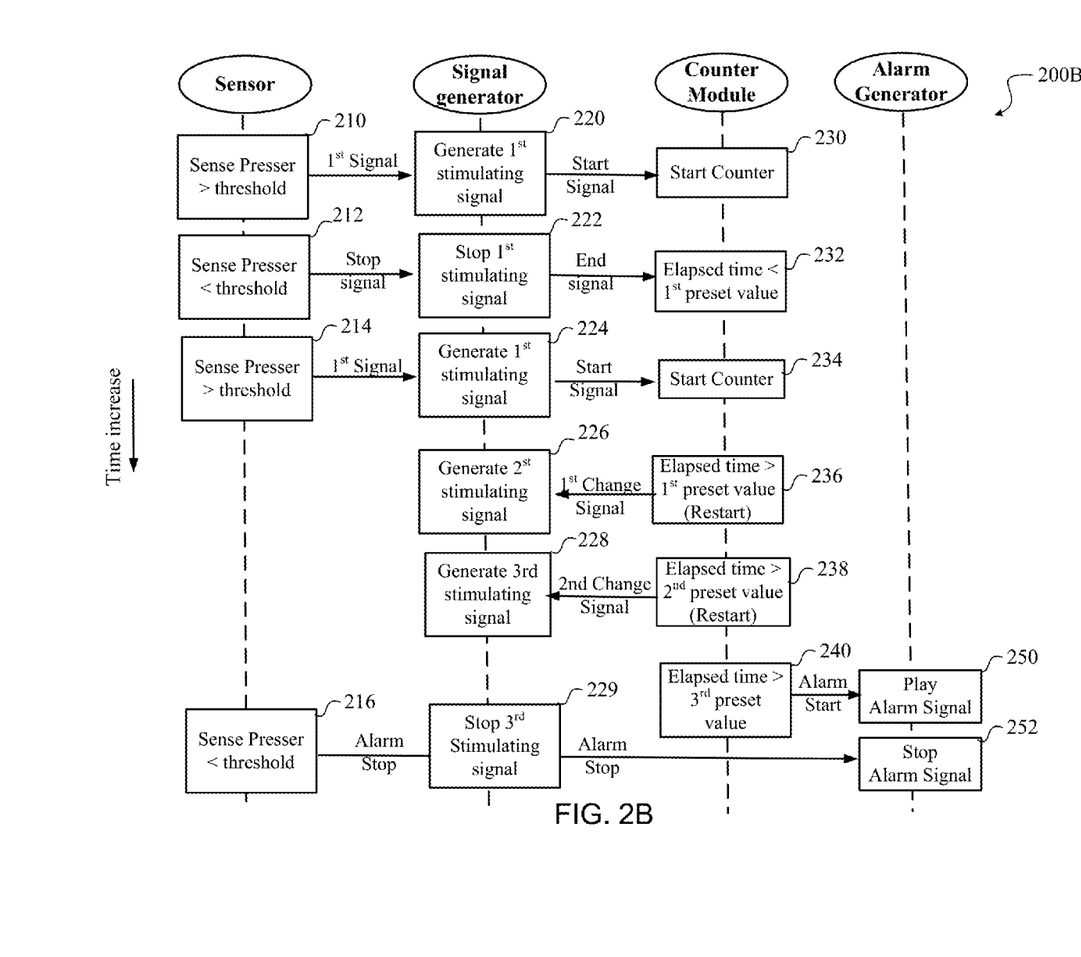
FIG. 2B is a time diagram illustrating an example of the functionality of the device for sleep apnea avoidance and data collection of FIG. 2A.

FIG. 2B is a time diagram 200B illustrating an example of the functionality of the device 100 for sleep apnea avoidance and data collection of FIG. 2A. The time diagram 200B shows the interaction between various components and modules of the device 100. Various operation blocks are executed as shown from top to the bottom of the diagram as the elapsed time increases. At operation block 210, the sensor 140 of FIG. 2A may sense a pressure exceeding the threshold set by the user of device 100, and in response, the sensor 140 may generate the first signal, which is received by the signal generator module 150 of FIG. 2A. At operation block 220, the signal generator module 150 may generate the first stimulating signal. At operation block 230, the counter module 194 may start counting the elapsed time after issuing of the start signal by the signal generator module 150, in response to the start signal received from the signal generator module 150.

At operation block 212, the sensor 140 may sense a pressure less than the threshold, which indicates that the user has changed sleeping position and is not sleeping over the device 100 any longer. The sensor 140 may then send a stop signal to the signal generator 150, and the signal generator 150 may stop the first stimulating signal, at operation block 212, and send an end signal to the counter module 194. The counter module 194, in response to the end signal, at operation 232, may determine the elapsed time, which in this case is determined to be less than the first preset value set by the user.

At operation block 214, the senor 140 may sense a pressure higher than the set threshold, and may send the first signal to the signal generator module 150, which in turn, at operation block 224, may generate the first stimulating signal and issue a start signal to the counter module 194. In this scenario, the user does not respond to the first stimulating signal and the counter determines, at operation block 236, that the elapse time after the start signal has exceeded the first preset value. The counter module 194, may restart and issue a first change signal, in response to which, the signal generator 150, at operation block 226, may start the second stimulating signal. The second stimulating signal may be different from the first stimulating signal, for example, having a different type of waveform, or being stronger in terms of magnitude, having a different frequency or duty cycle so that it is perceived by the user to be more stimulating or alerting.

If the user does not respond to the second stimulating signal and the counter module 194, at operation 238, determines that the elapsed time after the start of the second stimulating signal has surpassed a second preset value, the counter module 194 may restart and issue a second change signal to the signal generator 150. In response to the second change signal, the signal generator 150, at operation block 228, may start a third stimulating. The elapsed time form the start of the third stimulating signal may is measured by the counter module 194. At operation block 240, the counter module 194 may determine that the elapsed time after the start of the third stimulating signal has exceeded a third preset value.

At this time the counter module 194 may issue an alarm start signal that is received by the audio alarm generator 160 of FIG. 2A. The audio alarm generator 160, at operation block 250, may play an alarm signal, which can make the user to change sleeping position. The alarm sound may be configured not to awaken or awaken the user. Once the user changes the sleeping position, the sensor 140, at operation block 216, may sense the change in pressure and may send an alarm stop signal that is sensed by both the signal generator module 150 and the audio alarm generator 160. At operation block 229, the signal generator module 150 may stop the third stimulating signal, and at operation block 252, the audio alarm generator 160 may stop the audio alarm signal. There may be other similar scenarios of interaction between the various components that are not shown here for simplicity.

Figure 3A:
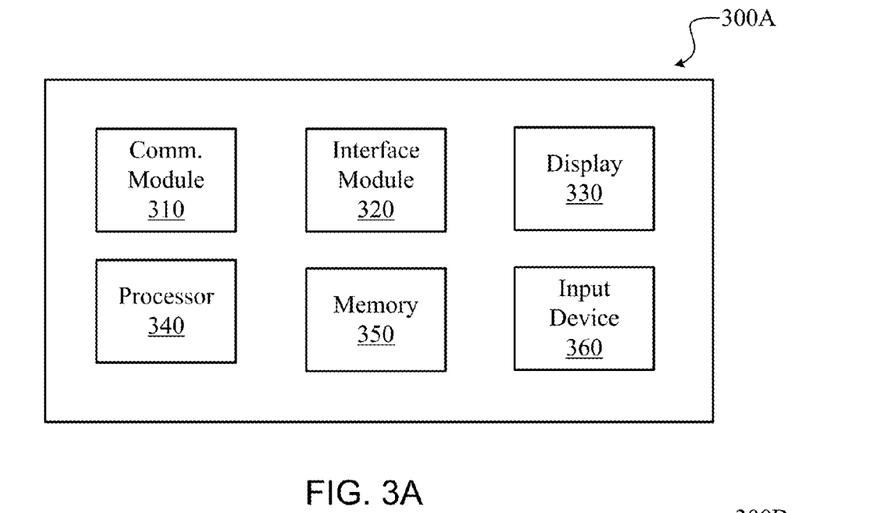
FIG. 3A is a block diagram illustrating an example structure of a device for communication with a sleep apnea avoidance and data collection device.

FIG. 3A is a block diagram illustrating an example structure of a device 300A for communication with a sleep apnea avoidance and data collection device 100 of FIG. 2A. The device 300A, referred to as the other (e.g., external) device herein, represents, for example, the handheld device 120 of FIG. 1B or the laptop computer 130 of FIG. 1B. The device 300A may include a communication circuit (also called "communication module") 310, an interface (also called "interface module") 320, a display 330, a processor 340, memory 350, and an input device 360.

The communication module 310 may communicate to the device 100 via a network such as a wireless network, including Wi-Fi, WLAN, PAN, WAN, and the like, via near-field-communication (NFC), or other network technologies. The communication module 310 may transmit information to the device 100; the information may be related to the use of a bed including the information indicating the bed as the designated bed and the first time that the designated bed is used by the user. The information may be related to the threshold set by the user using a first interface provided by the interface module 320 and displayed on the display 330. In some aspects, the information may be related to the selected first stimulating signal and may include a type, a magnitude, and other attributers of the selected stimulating signal that is selected by the user by employing a second user interface provided by the interface module 320. The information may further be related to an audio alarm set by the user using a third user interface provided by the interface module 320. Finally, the information related to an audio alarm including a type, a volume, and a trigger event. The trigger event may indicate a trigger event for activating the audio alarm, as discussed in more detail above.

The interface module 320 may provide other user interfaces for receiving other information from the user. The other information may be related to the second and third stimulating signals and the first and second preset values. The interface module 320 may provide user interfaces for communication of various information to the user of device 300A. For example, a user interface provided by interface module 320 and displayed on display 330 may be configured to display upon request from the user the collected data including the history information such as a date, a start time, and a stop time for each of the first, second, and third stimulating signals and the audio alarm signals that were generated, each time the device was used by the user, from the user of device 100. Display 330 may include a liquid crystal display (LCD) or a touch sensitive display. Processor 340 may be a general-purpose processor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information. Processor 340 may execute various applications and software modules stored in memory 350, for example, computer programs associated with the signal generator module 150, audio alarm generator 160, and monitoring module 190 of FIG. 2A.

In some aspects, various application and software modules such computer programs associated with the signal generator module 150, audio alarm generator 160, and monitoring module 190 may be stored on memory 350, which may include one or more machine-readable media. Memory 350 may include a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device. An input device 360 may include a keyboard, a mouse, a touch screen, or an audio input device that can receive input data from the user of device 300A. The inputs may be related to the device 100.

Figure 3B:
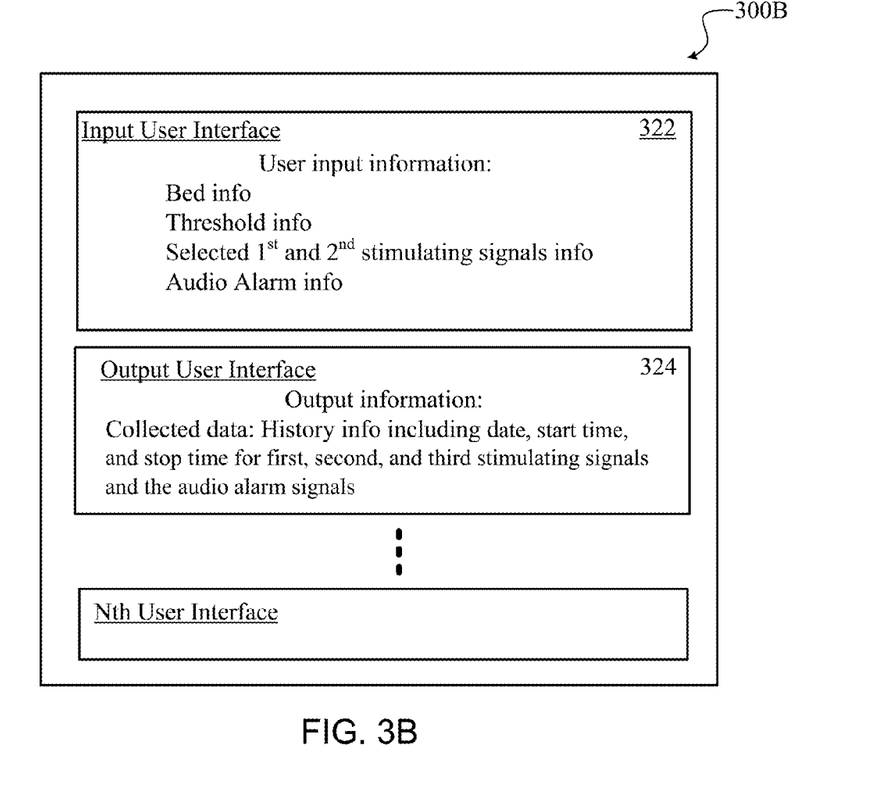
FIG. 3B is a block diagram illustrating an example user interface of the device of FIG. 3A.

FIG. 3B is a block diagram illustrating an example user interface 300B of the device 300A of FIG. 3A. The user interface 300B may be provided by the interface module 320 and displayed on display 330 of FIG. 3A. The user interface 300B may include a number (e.g., N) of user interfaces. For example, an input user interface 322 may receive input information from the user, as discussed above with respect to first, second, third, and other user interfaces. An output user interface 324 may present information to the user such as the collected data as discussed above. The collected data may be saved in the memory 350 of FIG. 3A. The user interface 300B may include other user interfaces that display additional information related to device 100 of FIG. 2A.

Figure 4:
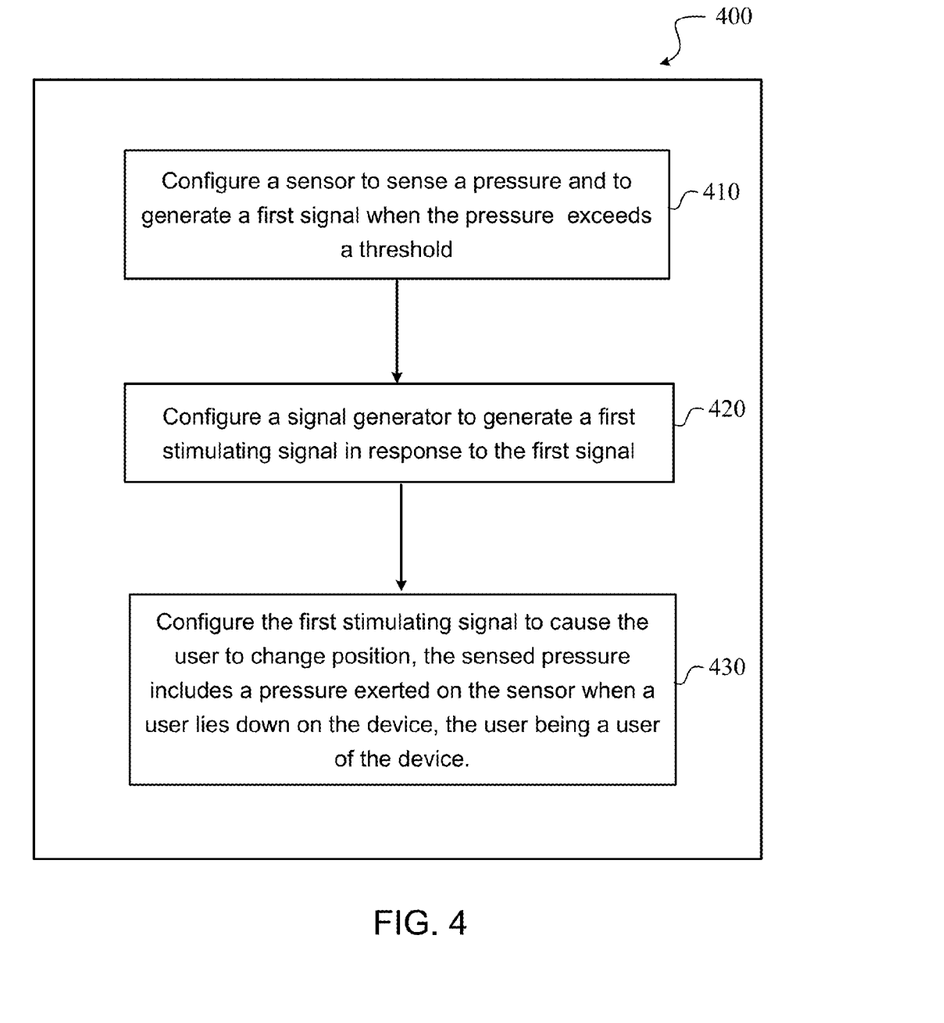
FIG. 4 is a flow diagram illustrating an example of a method for sleep apnea avoidance and data collection.

FIG. 4 is a flow diagram illustrating an example of a method 400 for sleep apnea avoidance and data collection. For explanatory purposes, the example method 400 is described herein with reference to sleep apnea avoidance and data collection device 100 of FIG. 2A; however, the example method 400 is not limited to the device 100. Further, for explanatory purposes, the blocks of the example method 400 are described herein as occurring in serial, or linearly. However, multiple blocks of the example method 400 may occur in parallel. In addition, the blocks of the example method 400 need not be performed in the order shown and/or one or more of the blocks of the example method 400 need not be performed.

At operation block 410, a sensor (e.g., 100 of FIG. 2A) may be configured to sense a pressure and to generate a first signal when the pressure exceeds a threshold. At operation block 420, a signal generator (e.g., 150 of FIG. 2A) may be configured to generate a first stimulating signal in response to the first signal. At operation block 430, the first stimulating signal may be configured to cause the user to change sleeping position from a first sleeping position to a second sleeping position as discussed above. The sensed pressure may include a pressure exerted on the sensor when a user of the device 100 lies down on the device 100.

In one example, the device 100 of FIG. 2A may comprise a computer memory, and each of the modules (e.g., 150, 160, 170, 180, and 190 of FIG. 2A) may include specific software code that can perform its respective specific action/function as described. In one example, the device 100 may comprise specific circuits and/or logic, and each of the modules (e.g., 150, 160, 170, 180, and 190) may comprise specific circuit component(s) or specific logic component(s) that can perform its respective specific action/function as described.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

1. A device for sleep apnea avoidance and data collection, comprising:

a sensor configured to sense a pressure and generate a first signal when the pressure exceeds a threshold; and a signal generator module configured to generate a first stimulating signal in response to the first signal, wherein, the sensed pressure includes a pressure exerted on the sensor when a user lies down on the device, the user being a user of the device, and the first stimulating signal is configured to cause the user to change sleeping position.

2. The device of clause 1, further comprising a threshold module configured to set the threshold when the user lies down on the device, for a first time, on a designated bed.

3. The device of clause 2 or any other clauses, further comprising a communication module configured to communicate with another device, wherein the other device includes at least one of a handheld device including a cellular phone, a tablet, and a personal assistant device (PDA), a laptop, or a desktop computer.

4. The device of clause 3 or any other clauses, wherein the communication module is further configured to receive information from the other device, the information including at least one of:

information related to a use of a bed including the information indicating the bed as the designated bed and the first time that the designated bed is used by the user, information related to the threshold set by the user using an first interface on the other device, information related to a selected first stimulating signal by the user using a second user interface on the other device, the information related to the selected first stimulating signal including at least one of a type or a magnitude of the selected stimulating signal, information related to an audio alarm signal set by the user using a third user interface on the other device, the information related to an audio alarm signal including at least one of a type, a volume, or a trigger event, wherein the trigger event indicate a trigger event for activating the audio alarm signal.

5. The device of clause 4 or any other clauses, wherein the signal generator module is further configured to:

stop generating the first stimulating signal in response to receiving a stop signal from the sensor when the user changes sleeping position from a first sleeping position that causes snoring to a second sleeping position that stops snoring;

generate the first stimulating signal based on the information related to the selected stimulating signal.

6. The device of clause 4 or any other clauses, further comprising an audio alarm signal generator configured to generate an audio alarm signal based on the information related to an audio alarm signal received from the other device, and one or more chargeable batteries, wherein the one or more chargeable batteries are configured to be charged wirelessly via the other device.

7. The device of clause 4 or any other clauses, further comprising a counter module configured to start measuring an elapsed time in response to the first signal, and to generate a first change signal when the elapsed time reaches a first preset value, to generate a second change signal when the elapsed time reaches a second preset value, and to generate an alarm start signal when the elapsed time reaches a third preset value.

8. The device of clause 7 or any other clauses, wherein the signal generator module is configured to generate, respectively, a second stimulating signal and a third stimulating signal in response to the first and second change signals received from the counter module, wherein the information related to the second and third stimulating signals and the first and second preset values are received from the other device and are provided by the user through one or more user interfaces, and wherein each of the first, second, and third stimulating signals are identified by at least one of a frequency, a duty cycle, a magnitude, or a type.

9. The device of clause 7 or any other clauses, wherein the communication module is further configured to transmit to the other device history information to be stored in the other device and to be displayed to the user upon request, the history information including a date, a start time, and a stop time for each of the first, second, and third stimulating signals and the audio alarm signals that were generated, each time the device was used by the user.

10. A method (e.g., 400 of FIG. 4) for sleep apnea avoidance and data collection using a device, the method comprising:

configuring a sensor to sense a pressure and to generate a first signal when the pressure exceeds a threshold (e.g., 410 of FIG. 4);

configuring a signal generator module to generate a first stimulating signal in response to the first signal (e.g., 420 of FIG. 4); and configuring the first stimulating signal to cause the user to change sleeping position (e.g., 430 of FIG. 4), wherein the sensed pressure includes a pressure exerted on the sensor when a user lies down on the device, the user being a user of the device, and the device including the sensor and the signal generator module.

11. The method of clause 10, further comprising configuring a threshold module to set the threshold when the user lies down on the device, for a first time, on a designated bed.

12. The method of clause 11 or any other clauses, further comprising configuring a communication module to communicate with another device, wherein the other device includes at least one of a handheld device including a cellular phone, a tablet, and a personal assistant device (PDA), a laptop, or a desktop computer.

13. The method of clause 12 or any other clauses, further comprising configuring the communication module to receive information from the other device, the information including at least one of:

information related to a use of a bed including the information indicating the bed as the designated bed and the first time that the designated bed is used by the user, information related to the threshold set by the user using an first interface on the other device, information related to a selected first stimulating signal by the user using a second user interface on the other device, the information related to the selected first stimulating signal including at least one of a type or a magnitude of the selected stimulating signal, information related to an audio alarm signal set by the user using a third user interface on the other device, the information related to an audio alarm signal including at least one of a type, a volume, or a trigger event, wherein the trigger event indicate a trigger event for activating the audio alarm signal.

14. The method of clause 13 or any other clauses, further comprising configuring the signal generator module to:

stop generating the first stimulating signal when the user changes sleeping position;

generate the first stimulating signal based on the information related to the selected stimulating signal.

15. The method of clause 13 or any other clauses, further comprising configuring an audio alarm generator to generate an audio alarm signal based on the information related to an audio alarm signal received from the other device.

16. The method of clause 13 or any other clauses, further comprising configuring a counter module to start measuring an elapsed time in response to the first signal, and to generate a first change signal when the elapsed time reaches a first preset value, and to generate a second change signal when the elapsed time reaches a second preset value.

17. The method of clause 16 or any other clauses, further comprising configuring the signal generator module to generate, respectively, a second stimulating signal and a third stimulating signal in response to the first and second change signals received from the counter module, wherein the information related to the second and third stimulating signals and the first and second preset values are received from the other device and are provided by the user through one or more user interfaces, and wherein each of the first, second, and third stimulating signals are identified by at least one of a frequency, a duty cycle, a magnitude, or a type.

18. The method of clause 16 or any other clauses, further comprising configuring the communication module to transmit to the other device history information to be stored in the other device and to be displayed to the user upon request, the history information including a date, a start time, and a stop time for each of the first, second, and third stimulating signals and the audio alarm signals that were generated, each time the device was used by the user.

19. A device for communicating with a sleep apnea avoidance device, the device comprising:
    a communication module configured to wirelessly communicate with the sleep apnea avoidance device; and
    an interface module configured to provide one or more user interfaces, wherein the user interfaces are configured to:
    receive user information from a user including a user of the sleep apnea prevention device, the inputs being for communication to the sleep apnea avoidance device; and
    display information received from the sleep apnea avoidance device, wherein the sleep apnea avoidance device comprises:
        a sensor configured to sense a pressure and generate a first signal when the pressure exceeds a threshold; and
        a signal generator module configured to generate a first stimulating signal in response to the first signal, wherein,
        the sensed pressure includes a pressure exerted on the sensor when a user lies down on the device, the user being a user of the device, and
        the first stimulating signal is configured to cause the user to change sleeping position.

20. The device of clause 19, further comprising memory to store at least a portion of the information received from the sleep apnea prevention device, wherein the user information includes at least one of:
    information related to a use of a bed including the information indicating the bed as a designated bed and a first time that the designated bed is used by the user,
    information related to a threshold used by a sensor of the sleep apnea prevention device,
    information related to a selected first stimulating signal including at least one of a type or a magnitude of the selected stimulating signal, the selected stimulated signal being used by a signal generator module of the sleep apnea avoidance device,
    information related to an audio alarm signal of the sleep apnea avoidance device including at least one of a type, a volume, or a trigger event, wherein the trigger event indicate a trigger event for activating the audio alarm signal.

Figure 5:
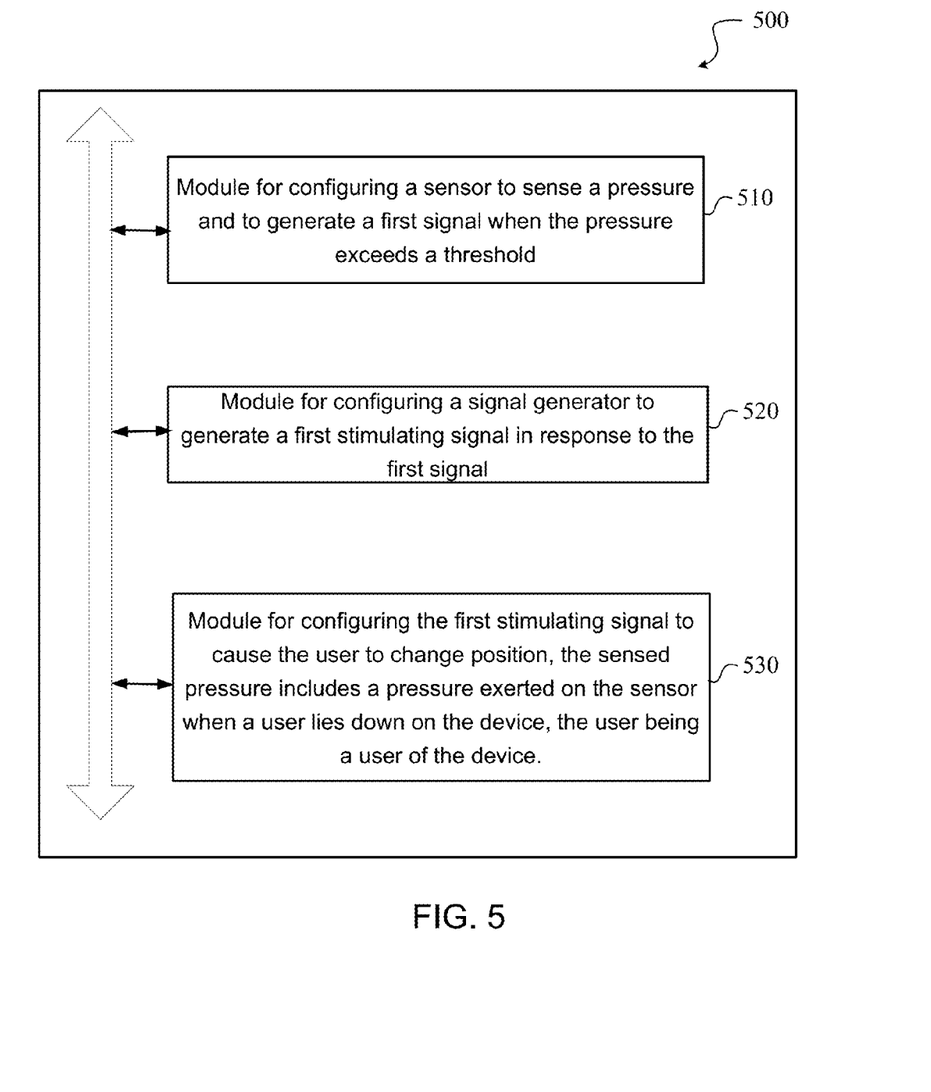
FIG. 5 is a diagram illustrating an example of an apparatus for sleep apnea avoidance and data collection.

21. An apparatus (e.g., apparatus 500 of FIG. 5) comprising:
    means for configuring a sensor to sense a pressure and to generate a first signal when the pressure exceeds a threshold (e.g., 510 of FIG. 5);
    means for configuring a signal generator module to generate a first stimulating signal in response to the first signal (e.g., 520 of FIG. 5); and
    means for configuring the first stimulating signal to cause the user to change sleeping position (e.g., 530 of FIG. 5), wherein the sensed pressure includes a pressure exerted on the sensor when a user lies down on the device, the user being a user of the device, and the device including the sensor and the signal generator module.

22. An apparatus comprising means for performing any of the method clauses 11-18.

Other Remarks

In one aspect, any of the clauses herein may depend from any one of the independent clauses or any one of the dependent clauses. In one aspect, any of the clauses (e.g., dependent or independent clauses) may be combined with any other clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

In one aspect, any methods, instructions, code, means, logic, components, blocks, modules and the like (e.g., software or hardware) described or claimed herein can be represented in drawings (e.g., flow charts, block diagrams), such drawings (regardless of whether explicitly shown or not) are expressly incorporated herein by reference, and such drawings (if not yet explicitly shown) can be added to the disclosure without constituting new matter. For brevity, some (but not necessarily all) of the clauses/descriptions/claims are explicitly represented in drawings, but any of the clauses/descriptions/claims can be represented in drawings in a manner similar to those drawings explicitly shown. For example, a flow chart can be drawn for any of the clauses, sentences or claims for a method such that each operation or step is connected to the next operation or step by an arrow. In another example, a block diagram can be drawn for any of the clauses, sentences or claims having means-for elements (e.g., means for performing an action) such that each means-for element can be represented as a module for element (e.g., a module for performing an action).

Those of skill in the art would appreciate that items such as the various illustrative blocks, modules, elements, components, methods, operations, steps, and algorithms described herein may be implemented as hardware or a combination of hardware and computer software.

To illustrate the interchangeability of hardware and software, items such as the various illustrative blocks, modules, elements, components, methods, operations, steps, and algorithms have been described generally in terms of their functionality. Whether such functionality is implemented as hardware or software depends upon the particular application and design constraints imposed on the overall system. Skilled artisans may implement the described functionality in varying ways for each particular application.

In one aspect, "means," a block, a module, an element, a component or a processor may be an item (e.g., one or more of blocks, modules, elements, components or processors) for performing one or more functions or operations. In one aspect, such an item may be an apparatus, hardware, or a portion thereof. In an example, an item may be implemented as one or more circuits configured to perform the function(s) or operation(s). A circuit may include one or more circuits and/or logic. A circuit may be analog and/or digital. A circuit may be electrical and/or optical. A circuit may include transistors. In an example, one or more items may be implemented as a processing system (e.g., a digital signal processor (DSP), an application specific integrated circuit (ASIC), a field programmable gate array (FPGA), etc.), a portion(s) or a combination(s) of any of the foregoing. In one example, an item may have a structure in the form of, for example, an instruction(s) encoded or stored on a machine-readable medium, on another device, or on a portion thereof. An instruction(s) may be software, an application(s), a subroutine(s), or a portion thereof for performing the function(s) or operation(s). The instruction(s) may be executable by one or more processors. Those skilled in the art will recognize how to implement the circuits, processing systems, instructions and a combination thereof.

In one aspect of the disclosure, when actions or functions (e.g., receiving, determining, providing, generating, configuring, displaying, communicating, transmitting, reporting, sending, or any other action or function) are described as being performed by an item (e.g., one or more of blocks, modules, elements, components or processors), it is understood that such actions or functions may be performed, for example, by the item directly. In another example, when an item is described as performing an action, the item may be understood to perform the action indirectly, for example, by facilitating such an action (e.g., assisting, allowing, enabling, causing, or providing for, such action to occur; or performing a portion of such an action). For example, determining can refer to facilitating determination, generating can refer to facilitating generating, and receiving can refer to facilitating receiving. In one aspect, performing an action may refer to performing a portion of the action (e.g., performing a beginning part of the action, performing an end part of the action, or performing a middle portion of the action).

A reference to an element in the singular is not intended to mean "one and only one" unless specifically so stated, but rather "one or more." For example, a first signal may refer to one or more first signals, a stimulating signal may refer to one or more stimulating signals, an alarm signal may refer to one or more alarm signals, a stop signal may refer to one or more stop signals, and a signal may refer to differential voltage signals.

Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, sleeping positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. In one aspect of the disclosure, the elements recited in the accompanying claims may be performed by one or more modules or sub-modules.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

The disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. §101, 102, or 103, nor should they be interpreted in such a way. Any unintended embracement of such subject matter is hereby disclaimed.

What is claimed is:

1. A wearable device for sleep apnea avoidance and data collection, the device comprising:
   a wearable packaging case;
   a communication circuit enclosed in the wearable packaging case and configured to communicate with an external device;
   a sensor enclosed in the wearable packaging case and configured to sense a pressure and generate a first signal when the pressure exceeds a threshold;
   a signal generator enclosed in the wearable packaging case and configured to generate a first stimulating signal in response to the first signal; and
   a threshold generator enclosed in the wearable packaging case and configured to generate the threshold when a user lies down on the device, for a first time, using a designated bed,
   wherein,
   the sensed pressure comprises a pressure exerted on the sensor when the user lies down on the device, the user being a user of the device,
   the first stimulating signal is configured to cause the user to change current sleeping position,
   the communication circuit is configured to receive information indicating a bed as the designated bed, information related to a first time use of the bed by the user, and a softness or firmness of the bed, wherein the threshold generator is configured to change the threshold when the softness or firmness of the bed changes.

2. The device of claim 1, wherein the communication circuit is further configured to receive, from the external device, first information regarding the first stimulating signal including a value of the threshold and values of a magnitude, a duty cycle, and a frequency of the first stimulating signal, and wherein the signal generator is configured to use the first information to generate the first stimulating signal having the same values of the magnitude, the duty cycle, and the frequency.

3. The device of claim 1, wherein the communication circuit is further configured to receive, from the external device, information related to an audio alarm signal set by the user using a third user interface on the external device, the information related to the audio alarm signal including at least one of an alarm signal type, a volume, or a trigger event for activation of the audio alarm signal.

4. The device of claim 3, further comprising an audio alarm signal generator enclosed in the wearable packaging case and configured to generate the audio alarm signal based on the information related to the audio alarm signal, received from the external device, and one or more chargeable batteries, wherein the one or more chargeable batteries are configured to be charged wirelessly via the external device.

5. The device of claim 1, wherein the signal generator is further configured to stop generating the first stimulating signal in response to receiving a stop signal from the sensor when the user changes sleeping position from a first sleeping position that causes snoring to a second sleeping position that stops snoring.

6. The device of claim 1, further comprising a counter enclosed in the wearable packaging case and configured to start measuring an elapsed time in response to the first signal, to generate a first change signal when the elapsed time reaches a first preset value, to generate a second change signal when the elapsed time reaches a second preset value, and to generate an alarm start signal when the elapsed time reaches a third preset value.

7. The device of claim 6, wherein the signal generator is configured to generate, respectively, a second stimulating signal and a third stimulating signal in response to the first and second change signals received from the counter, wherein information related to the second and third stimulating signals and the first and second preset values are received from the external device and are provided by the user through a first user interface and one or more additional user interfaces, and wherein each of the first, second, and third stimulating signals includes signal properties including a frequency, a duty cycle, a magnitude, and a stimulating signal type.

8. The device of claim 7, wherein the communication circuit is further configured to transmit to the external device history information to be stored in the external device and to be displayed to the user upon request, the history information including a date, a start time, and a stop time for each of the first, second, and third stimulating signals and an audio alarm signal that were generated, each time the device was used by the user.

9. A method for providing a wearable sleep apnea avoidance device, the method comprising:
   providing a wearable packaging case;
   providing a communication circuit enclosed in the wearable packaging case and configured to communicate with an external device;
   providing a sensor enclosed in the wearable packaging case and configured to sense a pressure and to generate a first signal when the pressure exceeds a threshold;
   providing a signal generator enclosed in the wearable packaging case and configured to generate a first stimulating signal in response to the first signal;
   providing a threshold generator enclosed in the wearable packaging case; and configuring the threshold generator to generate the threshold when a user lies down on the device, for a first time, using a designated bed, wherein the first stimulating signal is configured to cause the user to change sleeping position, wherein the sensed pressure comprises a pressure exerted on the sensor when the user lies down on the wearable sleep apnea avoidance device, the user being a user of the wearable sleep apnea avoidance device, and the wearable sleep apnea avoidance device including the sensor, the communication circuit, and the signal generator, wherein the method further comprises configuring the communication circuit to receive information indicating a bed as the designated bed, information related to a first time use of the bed by the user, and a softness or firmness of the bed, wherein the threshold generator is configured to change the threshold when the softness or firmness of the bed changes.

10. The method of claim 9, further comprising:
configuring the communication circuit to receive first information regarding the first stimulating signal including a value of the threshold and values of a magnitude, a duty cycle, and a frequency of the first stimulating signal; and
configuring the signal generator to use the first information to generate the first stimulating signal having the same values of the magnitude, the duty cycle, and the frequency.

11. The method of claim 9, wherein the external device includes at least one of a handheld device, a laptop, or a desktop computer.

12. The method of claim 9, further comprising configuring the communication circuit to receive information related to an audio alarm signal set by the user using a third user interface on the external device, the information related to the audio alarm signal including at least one of an alarm signal type, a volume, or a trigger event for activating the audio alarm signal.

13. The method of claim 12, further comprising configuring an audio alarm generator to generate the audio alarm signal based on the information related to the audio alarm signal received from the external device.

14. The method of claim 9, further comprising configuring the signal generator to stop generating the first stimulating signal in response to receiving a stop signal from the sensor when the user changes the sleeping position from a first sleeping position that causes snoring to a second sleeping position that stops snoring.

15. The method of claim 9, further comprising configuring a counter to start measuring an elapsed time in response to the first signal, to generate a first change signal when the elapsed time reaches a first preset value, and to generate a second change signal when the elapsed time reaches a second preset value.

16. The method of claim 15, further comprising configuring the signal generator to generate, respectively, a second stimulating signal and a third stimulating signal in response to the first and second change signals received from the counter, wherein information related to the second and third stimulating signals and the first and second preset values are received from the external device and are provided by the user through a first user interface and one or more additional user interfaces, and wherein each of the first, second, and third stimulating signals includes signal properties including a frequency, a duty cycle, a magnitude, and a stimulating signal type.

17. The method of claim 16, further comprising configuring the communication circuit to transmit to the external device history information to be stored in the external device and to be displayed to the user upon request, the history information including a date, a start time, and a stop time for each of the first, second, and third stimulating signals and an audio alarm signal that were generated, each time the device was used by the user.

18. A system comprising:
a wearable sleep apnea avoidance device comprising:
a wearable packaging case;
a first communication circuit enclosed in the wearable packaging case and configured to communicate with a communication device;
a sensor enclosed in the wearable packaging case and configured to sense a pressure and generate a first signal when the pressure exceeds a threshold;
a signal generator enclosed in the wearable packaging case and configured to generate a first stimulating signal in response to the first signal; and
a threshold generator configured to generate the threshold when a user lies down on the device, for a first time, using a designated bed,
wherein,
the threshold generator is configured to change the threshold when a softness or firmness of the designated bed changes,
the sensed pressure comprises a pressure exerted on the sensor when the user lies down on the wearable sleep apnea avoidance device, the user being a user of the wearable sleep apnea avoidance device,
the first stimulating signal is configured to cause the user to change sleeping position, and
the communication device for communicating with the wearable sleep apnea avoidance device, the communication device comprising:
a second communication circuit configured to wirelessly communicate with the wearable sleep apnea avoidance device; and
an interface configured to provide one or more user interfaces, wherein the user interfaces are configured to:
receive inputs including user information from one or more users including the user of the wearable sleep apnea avoidance device, the inputs being for communication to the wearable sleep apnea avoidance device; and
display information received from the wearable sleep apnea avoidance device.

19. The system of claim 18, wherein the communication device comprises memory to store at least a portion of the information received from the wearable sleep apnea avoidance device, wherein the user information further includes information related to a use of a bed including information indicating the bed as the designated bed and the first time that the bed is used by the user.

20. The system of claim 18, wherein the communication device further comprises memory to store at least a portion of the information received from the wearable sleep apnea avoidance device, and wherein the information received from the wearable sleep apnea avoidance device is related to an audio alarm signal of the wearable sleep apnea avoidance device including at least one of an audio alarm signal type, a volume, or a trigger event for activating the audio alarm signal.

* * * * *